United States Patent
Leo

(10) Patent No.: US 11,154,364 B2
(45) Date of Patent: Oct. 26, 2021

(54) ROLL-SENSING SENSOR ASSEMBLY

(71) Applicant: St. Jude Medical International Holding S.à r.l., Luxembourg (LU)

(72) Inventor: Giovanni Leo, Cologny (CH)

(73) Assignee: St. Jude Medical Ineternational Holding S.à r.l., Luxembourg (LU)

( * ) Notice: Subject to any disclaimer, the term of this patent is extended or adjusted under 35 U.S.C. 154(b) by 788 days.

(21) Appl. No.: 15/747,536

(22) PCT Filed: Jul. 29, 2016

(86) PCT No.: PCT/IB2016/054585
§ 371 (c)(1),
(2) Date: Jan. 25, 2018

(87) PCT Pub. No.: WO2017/017659
PCT Pub. Date: Feb. 2, 2017

(65) Prior Publication Data
US 2018/0214215 A1    Aug. 2, 2018

Related U.S. Application Data

(60) Provisional application No. 62/198,892, filed on Jul. 30, 2015.

(51) Int. Cl.
| | |
|---|---|
| *A61B 5/06* | (2006.01) |
| *A61B 34/20* | (2016.01) |
| *A61B 5/00* | (2006.01) |
| *A61B 5/283* | (2021.01) |
| *A61B 5/287* | (2021.01) |
| *A61B 18/14* | (2006.01) |
| *A61B 18/00* | (2006.01) |

(52) U.S. Cl.
CPC ............. *A61B 34/20* (2016.02); *A61B 5/065* (2013.01); *A61B 5/283* (2021.01); *A61B 5/287* (2021.01); *A61B 5/6852* (2013.01); *A61B 18/1492* (2013.01); *A61B 2018/00351* (2013.01); *A61B 2018/00577* (2013.01); *A61B 2034/2051* (2016.02)

(58) Field of Classification Search
CPC ............ A61B 5/062; A61B 5/061–063; A61B 5/065–066; A61B 5/068
USPC ............... 600/372–375, 377, 380–381, 393, 600/422–427, 431, 466–468, 508–509; 606/20–52; 607/115, 119, 122–123
See application file for complete search history.

(56) References Cited

U.S. PATENT DOCUMENTS

| | | |
|---|---|---|
| 6,593,884 B1 | 7/2003 | Gilboa et al. |
| 7,197,354 B2 | 3/2007 | Sobe |
| 7,263,397 B2 | 8/2007 | Hauck et al. |

(Continued)

FOREIGN PATENT DOCUMENTS

| | | |
|---|---|---|
| EP | 1743575 A2 | 1/2007 |
| WO | 2012103304 A1 | 2/2012 |
| WO | 2013039564 A2 | 3/2013 |

*Primary Examiner* — Joseph A Stoklosa
*Assistant Examiner* — Brian M Antiskay
(74) *Attorney, Agent, or Firm* — Dykema Gossett PLLC

(57) ABSTRACT

A roll-sensing sensor assembly comprises an elongate body defining a first axis. A plurality of electrodes can be disposed about the first axis. A coil can extend along and be disposed about a second axis. In some embodiments, a canting plane of a loop in the coil is nonzero relative to a line perpendicular to and extending from the first axis.

20 Claims, 7 Drawing Sheets

(56) References Cited

U.S. PATENT DOCUMENTS

| | | | |
|---|---|---|---|
| 8,137,343 B2 * | 3/2012 | Harlev | A61B 34/20 |
| | | | 606/41 |
| 2002/0065455 A1 * | 5/2002 | Ben-Haim | A61B 5/145 |
| | | | 600/407 |
| 2003/0078509 A1 * | 4/2003 | Panescu | A61B 8/0833 |
| | | | 600/509 |
| 2007/0016007 A1 * | 1/2007 | Govari | A61B 5/0538 |
| | | | 600/424 |
| 2009/0018497 A1 * | 1/2009 | Birchard | A61B 5/062 |
| | | | 604/95.01 |
| 2009/0163810 A1 | 6/2009 | Kanade et al. | |
| 2009/0264738 A1 * | 10/2009 | Markowitz | A61B 5/063 |
| | | | 600/424 |
| 2010/0324412 A1 | 12/2010 | Govari et al. | |
| 2011/0158488 A1 | 6/2011 | Cohen et al. | |
| 2012/0150022 A1 * | 6/2012 | Bar-Tal | A61B 5/063 |
| | | | 600/424 |
| 2012/0172713 A1 * | 7/2012 | Carbonera | A61B 5/6855 |
| | | | 600/424 |
| 2012/0172716 A1 * | 7/2012 | Sela | A61B 5/062 |
| | | | 600/424 |
| 2013/0169272 A1 | 7/2013 | Eichler et al. | |
| 2013/0303944 A1 | 11/2013 | Duindam | |
| 2015/0272667 A1 * | 10/2015 | Govari | A61B 18/1492 |
| | | | 606/41 |
| 2016/0220117 A1 * | 8/2016 | Herken | A61B 5/065 |

* cited by examiner

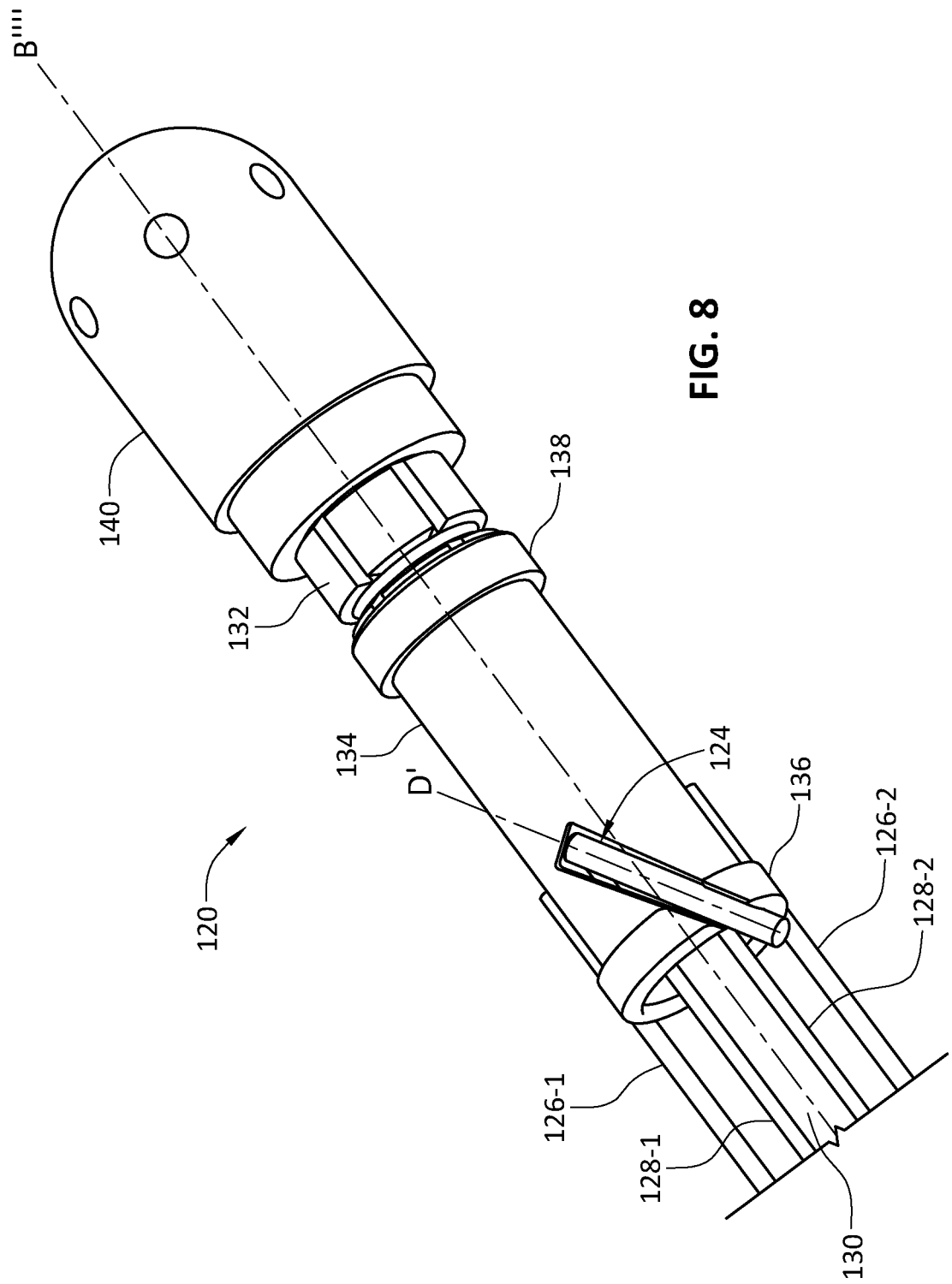

ROLL-SENSING SENSOR ASSEMBLY

CROSS-REFERENCE TO RELATED APPLICATION

This application claims priority to U.S. provisional patent application No. 62/198,892 entitled "ROLL-SENSING SENSOR ASSEMBLY," filed 30 Jul. 2015, which is hereby incorporated by reference as though fully set forth herein.

BACKGROUND a. Field

The present disclosure relates generally to a sensor assembly for a medical device, and more specifically to a sensor assembly that can sense roll. The sensor assembly comprises an electromagnetic position sensor and a plurality of electrodes.

b. Background

Medical devices such as guidewires, catheters, introducers and the like that include electromagnetic coil position sensors or electrodes for device navigation are used in various medical procedures in the body. For example, it is known to equip a catheter with multiple coils sufficient to allow a position sensing system to detect six (6) degrees-of-freedom (DOF), namely, a three-dimensional (3D) position (X, Y, Z) and a 3D orientation (e.g., roll, pitch, yaw) thereof. However, the design of a coil assembly that can provide such functionality provides challenges, particularly with respect to space constraints.

One known electromagnetic position sensor includes a coil wound symmetrically on a tubular core. Such a sensor may be seen by reference to U.S. Pat. No. 7,197,354, entitled "System for Determining the Position and Orientation of a Catheter" issued to Sobe, hereby incorporated by reference in its entirety as though fully set forth herein. Sobe discloses a core that is hollow, is symmetric about a central axis, and can be scaled in length, inner diameter, and outer diameter for a particular application. A coil is wound on the core in a desired winding pattern. The coil, like the core, is symmetric about the central axis. The sensor can be used in a system to detect position in 3D space defined by three perpendicular axes (X, Y, and Z), as well as rotation about two of the three axes (e.g., pitch and yaw), but the coil cannot detect rotation about the central axis of the core (e.g., roll). Accordingly, a medical device that incorporates a single sensor coil mounted symmetric about the central axis of the medical device only senses five (5) DOF, that is, two orientation parameters, in addition to three position parameters. Despite the DOF limitation, there are nonetheless desirable aspects of the above configuration. For example, the configuration uses minimal space and accommodates an open central lumen.

Electrode mapping systems, particularly those employing EnSite™ NavX™ navigation and visualization technology, such as EnSite™ Velocity™ cardiac mapping system of St. Jude Medical, utilize an electrical field to localize a medical device within a patient's body. The EnSite™ NavX™ system, is commercially offered by St. Jude Medical, Inc. and described in U.S. Pat. No. 7,263,397 to Hauck et al., which is hereby incorporated by reference in its entirety for all purposes. As is known, electrodes can be disposed in a spaced apart relationship about an axis of a catheter shaft. The electrodes can detect the electrical field generated by the NavX system and thereby detect position in 3D space defined by three perpendicular axes (X, Y, and Z), as well as rotation about two of the three axes (e.g., pitch and yaw), but the electrodes cannot detect rotation about the central axis of the catheter shaft (e.g., roll).

Known solutions for sensing the roll of a medical device generally involve using multiple sensors, each with a single coil as described above. For example, both U.S. Patent Application Publication No. 2010/0324412, entitled "Catheter With Obliquely-Oriented Coils," and U.S. Pat. No. 6,593,884, entitled "Intrabody Navigation System for Medical Applications," both of which are hereby incorporated by reference in their entireties as though fully set forth herein, teach placing separate sensors in different locations in a medical device with their respective coils oriented at different angles. Such configurations are more expensive and require more space in a medical device than a unitary sensor on a single core.

SUMMARY

Various embodiments herein provide a roll-sensing sensor assembly for a medical device. In at least one embodiment, a medical device can comprise an elongate body defining a first axis (e.g., a catheter longitudinal axis). A plurality of electrodes can be disposed about the first axis. A coil can extend along and be disposed about a second axis. In some embodiments, a canting plane of a loop in the coil is nonzero relative to a line perpendicular to and extending from the first axis.

In at least one embodiment, a medical device sensor assembly can comprise a plurality of electrodes that are disposed about an axis. A coil can extend along and be disposed about the axis. In some embodiments, the coil comprises a winding angle that is nonzero relative to a line perpendicular to and extending from the axis.

In at least one embodiment, a medical device sensor assembly can comprise an elongate catheter having a first axis. A plurality of electrodes can be disposed about the first axis. An electromagnetic sensor can extend along and be disposed about a second axis. In some embodiments, the second axis can be disposed at a placement angle that is nonzero relative to the first axis and less than 90 degrees relative to the first axis.

In at least one embodiment, a medical device can comprise an elongate body. A plurality of electrodes can be coupled to the elongate body and configured to produce a first position and orientation signal indicative of five degrees of freedom in response to an applied electrical field. An electromagnetic sensor can be coupled to the elongate body and can be configured to produce a second position and orientation signal indicative of five degrees of freedom in response to an applied magnetic field. The first and second position and orientation signals can be combinable to determine a position and orientation indicative of six degrees of freedom.

BRIEF DESCRIPTION OF THE DRAWINGS

FIG. 8 is an isometric view of an embodiment similar to that depicted in FIG. 7, in accordance with embodiments of the present disclosure.

DETAILED DESCRIPTION

Figure 1:
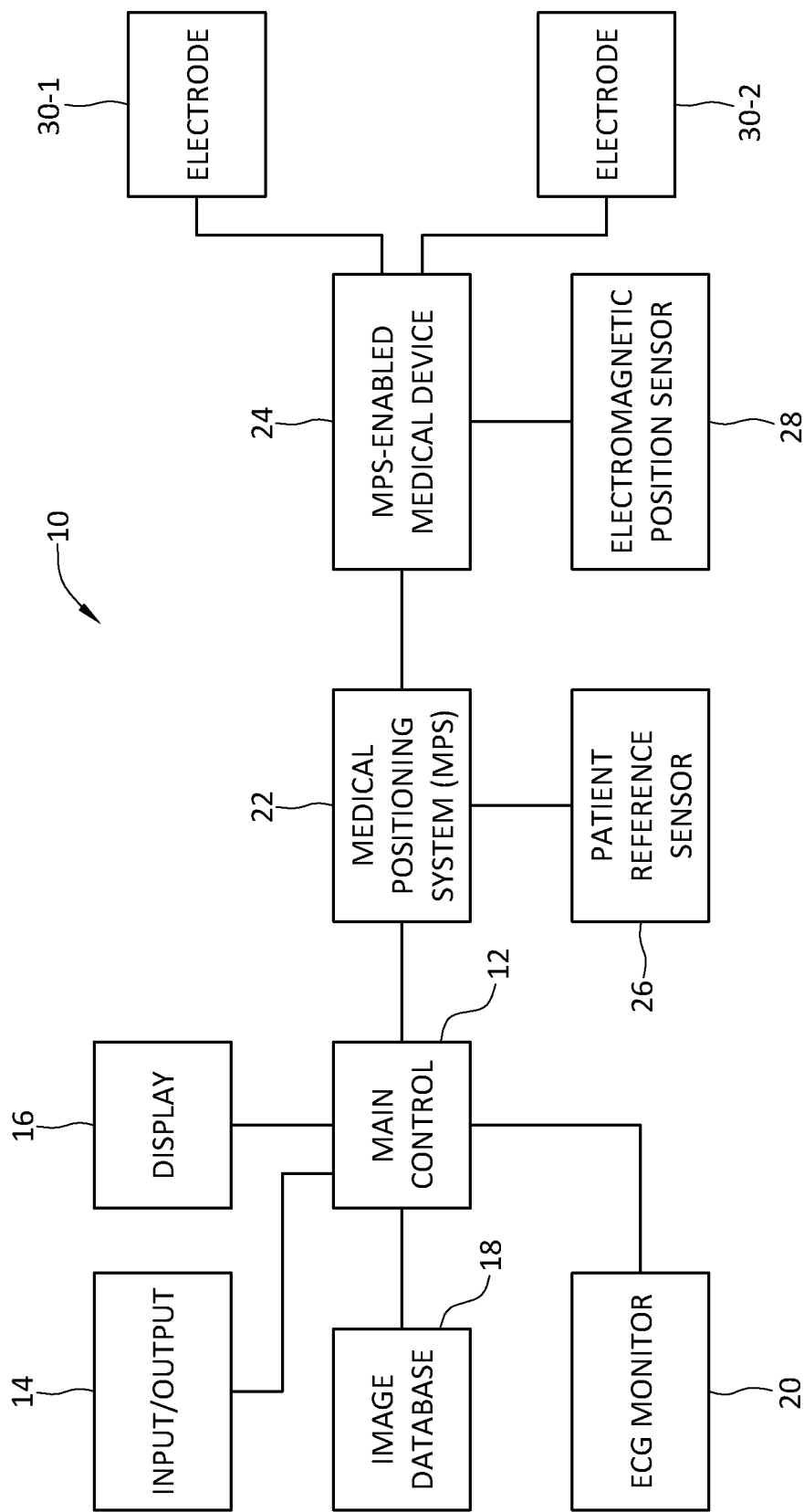
FIG. 1 is a schematic and block diagram view of a system incorporating an embodiment of a position-sensing medical device, in accordance with embodiments of the present disclosure.

Referring now to the drawings wherein like reference numerals are used to identify identical or similar components in the various views, FIG. 1 is a diagrammatic view of a system 10 in which a medical device, such as a guidewire, catheter, introducer (e.g., sheath) incorporating an electromagnetic position sensor and a plurality of electrodes may be used.

Before proceeding to a detailed description of the embodiments of the present disclosure, a description of an exemplary environment in which such devices and sensors may be used will first be set forth. With continued reference to FIG. 1, system 10 as depicted includes a main electronic control unit 12 (e.g., a processor) having various input/output mechanisms 14, a display 16, an optional image database 18, an electrocardiogram (ECG) monitor 20, a localization system such as a medical positioning system (MPS) 22, an MPS-enabled elongate medical device 24, a patient reference sensor 26, an electromagnetic position sensor 28 and a plurality of electrodes 30-1, 30-2, hereinafter referred to as electrodes 30.

Input/output mechanisms 14 may comprise conventional apparatus for interfacing with a computer-based control unit including, for example, one or more of a keyboard, a mouse, a tablet, a foot pedal, a switch and/or the like. Display 16 may also comprise conventional apparatus, such as a computer monitor. The main electronic control unit 12 can be a combination of hardware and program instructions configured to perform a number of functions. The hardware, for example, can include one or more processing resources, computer readable medium (CRM), etc. The program instructions (e.g., computer-readable instructions (CRI)) can include instructions stored on the CRM and executable by the processing resource to implement desired functions, as discussed herein (e.g., determine a position and orientation indicative of six degrees of freedom from a first position and orientation signal from a plurality of electrodes indicative of five degrees of freedom and a second position and orientation signal from a magnetic sensor indicative of five degrees of freedom, etc.). The CRI can also be stored in remote memory managed by a server and represent an installation package that can be downloaded, installed, and executed. The main control 12 can include memory resources, and the processing resources can be coupled to the memory resources.

The processing resources can execute the CRI that can be stored on an internal or external non-transitory CRM. The processing resources can execute the CRI to perform various functions, including the functions described with respect to FIGS. 1 to 8.

Various embodiments described herein may find use in navigation applications that use real-time and/or pre-acquired images of a region of interest. Therefore, system 10 may optionally include image database 18 to store image information relating to the patient's body. Image information may include, for example, a region of interest surrounding a destination site for medical device 24 and/or multiple regions of interest along a navigation path contemplated to be traversed by medical device 24. The data in image database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 20. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 20 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 12 for ECG synchronized play-back of a previously captured sequence of images (cine loop) stored in database 18. ECG monitor 20 and ECG-electrodes may both comprise conventional components.

MPS 22 is configured to serve as the localization system and to determine position (localization) data with respect to one or more electromagnetic position sensors 28 and plurality of electrodes 30 and output a respective location reading. The location readings may each include at least one or both of a position and an orientation (P&O) relative to a reference coordinate system, which may be the coordinate system of MPS 22. For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of an electromagnetic position sensor 28 in a magnetic field relative to a magnetic field generator(s) or transmitter(s) and/or a plurality of electrodes 30 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

MPS 22 determines respective locations (e.g., P&O) in the reference coordinate system based on capturing and processing signals received from the electromagnetic position sensor 28 while the sensor is disposed in a controlled low-strength alternating current (AC) magnetic (e.g., electromagnetic) field and signals received from the plurality of electrodes 30 while the electrodes are disposed in a controlled electrical field generated by electrode patches, for example. It should be noted that although only one electromagnetic sensor 28 is shown, MPS 22 may determine P&O for multiple electromagnetic sensors 28. In addition, although only two electrodes are shown, MPS 22 may determine P&O for multiple electrodes.

As discussed in more detail below, each electromagnetic position sensor 28 and the like may comprise a coil and, from an electromagnetic perspective, the changing or AC magnetic field may induce a current in the coil(s) when the coil(s) are in the magnetic field. The electromagnetic position sensor 28 is thus configured to detect one or more characteristics (e.g., flux) of the magnetic field(s) in which it is disposed and generate a signal indicative of those characteristics, which is further processed by MPS 22 to obtain a respective P&O for the electromagnetic sensor 28. Each of the electrodes 30 may comprise a ring electrode, in some examples. The electrodes 30 can be configured to detect one or more characteristics (e.g., current) of the electrical field(s) in which they are disposed and generate a signal indicative of those characteristics, which is further processed by MPS 22 to obtain a respective P&O for the plurality of electrodes 30. The respective P&O information for the electromagnetic position sensor 28 and the electrodes 30 can be analyzed together to express the P&O of the MPS-enabled medical device 24 with six DOF. Exemplary six-DOF sensors are more fully described herein.

Referring still to FIG. 1, in an embodiment, MPS 22 may determine the P&O of MPS enabled medical device 24 according to certain physical characteristics of electromagnetic position sensor 28 and electrodes 30 in addition to the signals received from sensor 28 and electrodes 30. Such characteristics may include predetermined calibration data, for example, indicative of or corresponding to the respective winding angles of one or more portions of a coil on sensor 28, the number of coil portions, the type(s) of conductor used in the coil, and the direction and number of loops in the coil. In addition, such characteristics may include predetermined calibration data, for example, indicative of or corresponding to a position of electrodes 30, the number of electrodes 30, size of electrodes 30, shape of electrodes 30, and type of material(s) the electrodes are formed of. MPS 22 may have such characteristics of the electromagnetic position sensor 28 and/or electrodes 30 pre-programmed, may determine such characteristics from a calibration procedure, or may receive such characteristics from a storage element coupled with medical device 24.

Electromagnetic position sensor 28 and the plurality of electrodes 30 may be associated with MPS-enabled medical device 24. Another MPS sensor, namely, patient reference sensor (PRS) 26 (if provided in system 10) can be configured to provide a positional reference of the patient's body so as to allow motion compensation for patient body movements, such as respiration-induced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. PRS 26 may be attached to the patient's manubrium sternum or other location. Like the electromagnetic position sensor 28, PRS 26 can be configured to detect one or more characteristics of the magnetic field in which it is disposed, wherein MPS 22 determines a location reading (e.g., a P&O reading) indicative of the PRS's position and orientation in the reference coordinate system. In some embodiments, an additional PRS can be configured to detect one or more characteristics of the electrical field in which it is disposed, wherein the MPS 22 determines a location reading (e.g., a P&O reading) indicative of the PRS's position and orientation in the reference coordinate system.

Figure 2:
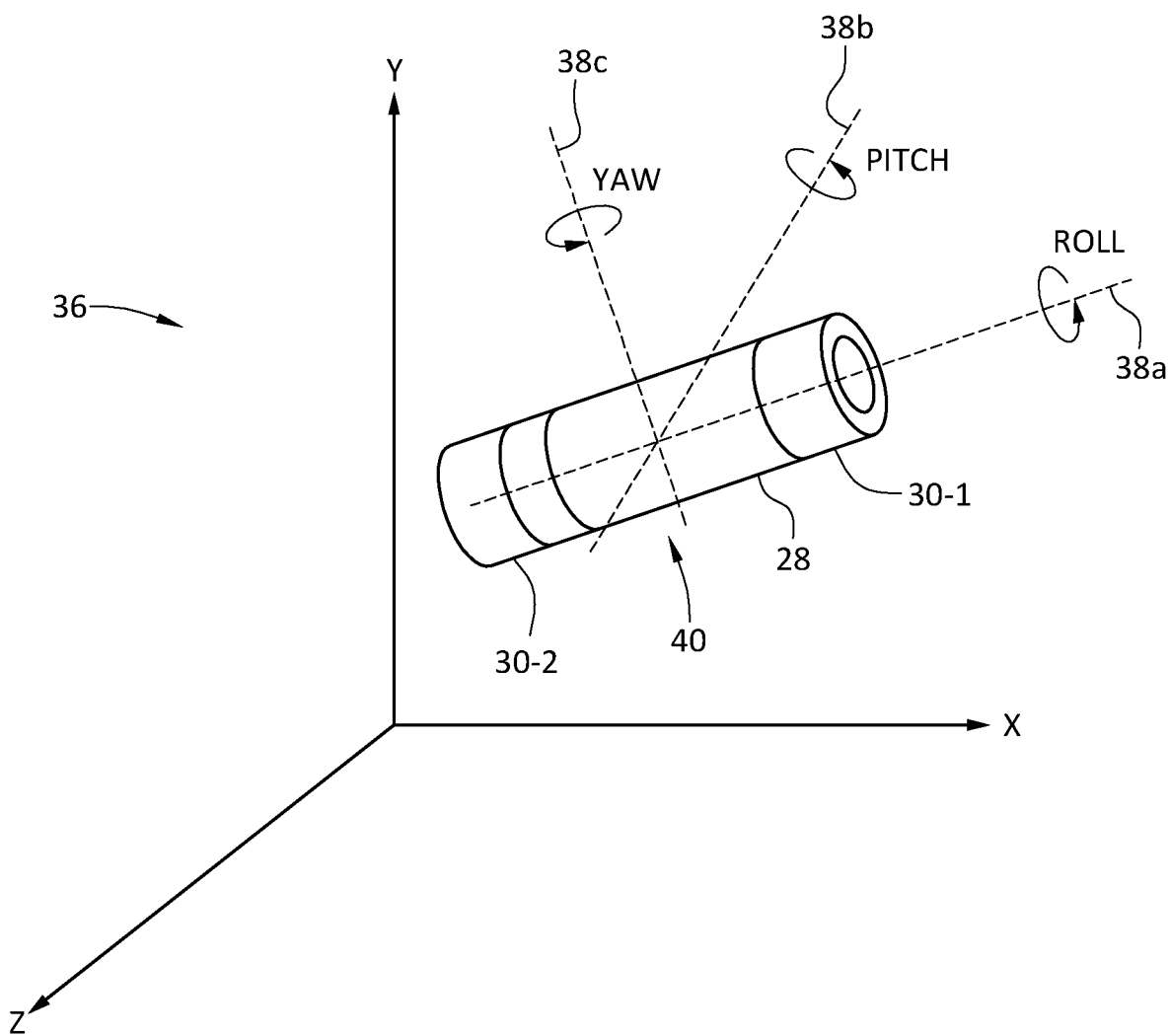
FIG. 2 is a diagrammatic view of an embodiment of a roll-sensing sensor assembly in the coordinate system of a medical positioning system, in accordance with embodiments of the present disclosure.
Figure 5A:
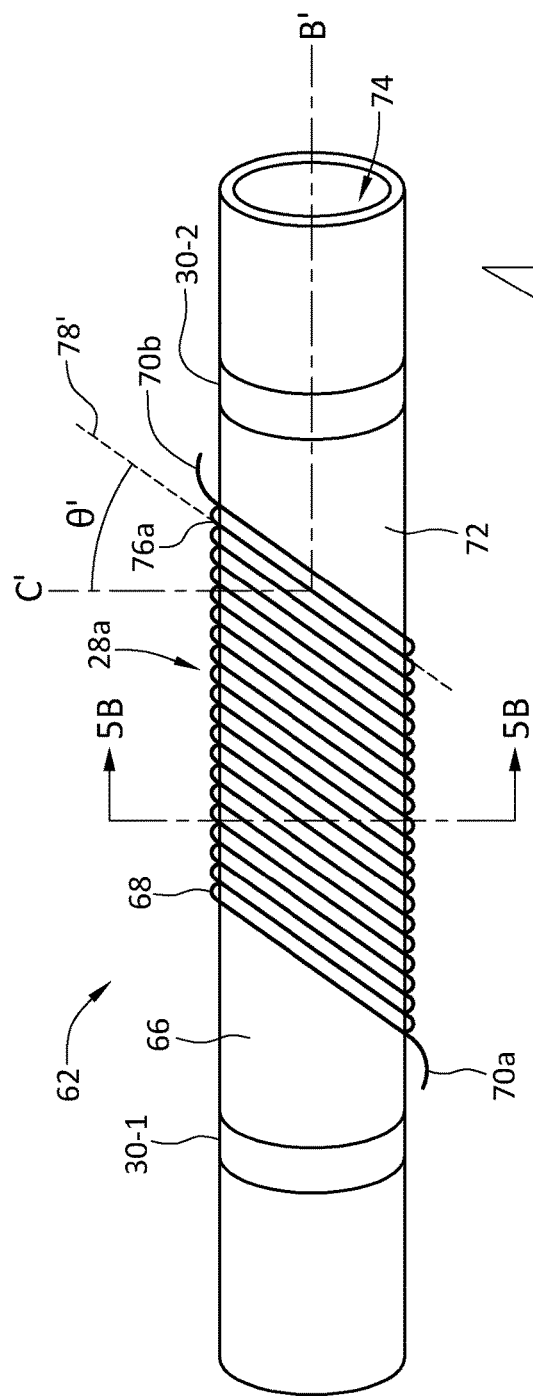
FIG. 5A is a schematic isometric view of an embodiment of a roll-sensing sensor assembly, in accordance with embodiments of the present disclosure.
Figure 6:
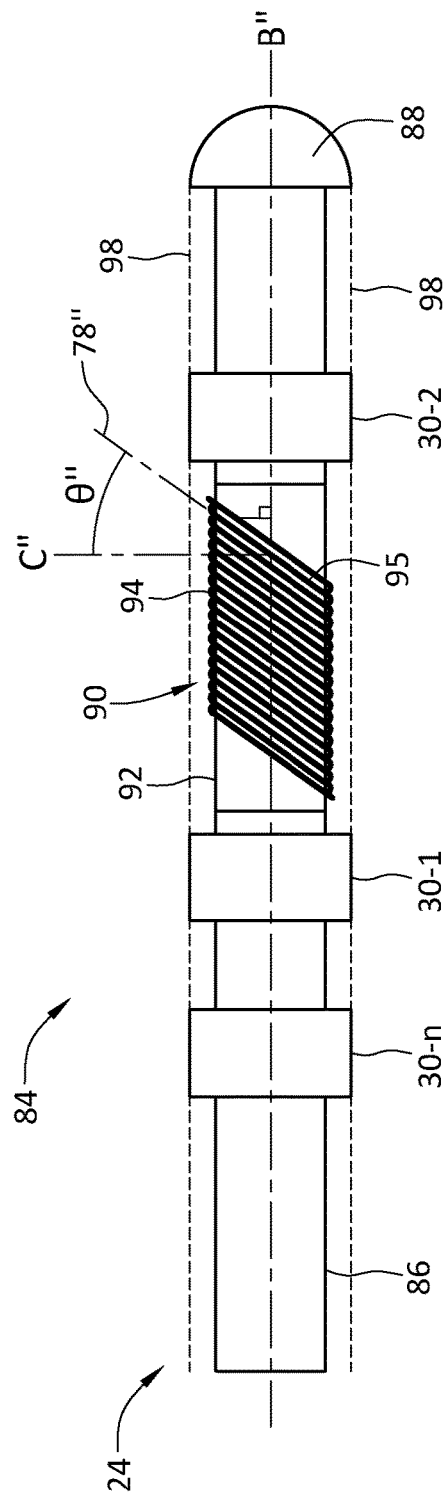
FIG. 6 is a side view of a medical device comprising a roll-sensing sensor assembly, in accordance with embodiments of the present disclosure.
Figure 7:
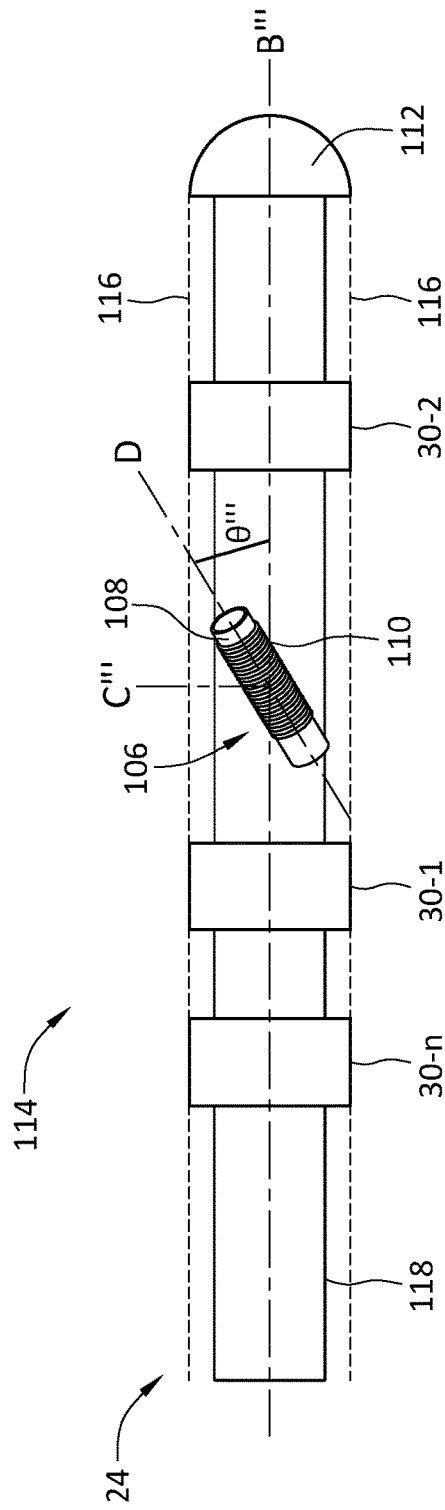
FIG. 7 is a side view of another embodiment comprising a roll-sensing sensor assembly, in accordance with embodiments of the present disclosure.

FIG. 2 is a diagrammatic view of a roll-sensing sensor assembly 40 that comprises an electromagnetic position sensor 28 and a plurality of electrodes 30, in the coordinate system 36 of MPS 22. The roll-sensing sensor assembly 40 can include an electromagnetic position sensor 28 (e.g., coil wound about an axis of the roll sensing sensor assembly 40, as depicted in FIGS. 5A-6 and/or a coil connected to the roll sensing sensor assembly 40, as depicted in FIG. 7) and a plurality of electrodes 30 disposed about the axis of the roll sensing sensor assembly. In some embodiments, the electrodes 30 can be ring electrodes. The position of the roll-sensing sensor assembly can be determined by MPS 22 with respect to the three axes (X, Y, Z) of a coordinate system that are set relative to a piece of hardware, such as a magnetic field generator and electrical field generator. The orientation angles (e.g., for roll, pitch, and yaw) of the roll-sensing sensor assembly 40 can also be determined by MPS 22, taken with respect to the origin.

The roll-sensing sensor assembly 40 can be disposed along an axis of the medical device 24. For example, an axis of the roll-sensing sensor assembly 40, defined as extending through the electrodes (e.g., ring electrodes) can be parallel and collinear with the axis of the medical device 24. For a medical device 24 that includes the roll-sensing sensor assembly 40, "roll" refers to rotation about the axis 38$a$ along which the roll-sensing sensor assembly 40 extends. "Pitch" and "yaw" respectively refer to rotation about axes that bisect the roll-sensing sensor assembly 40 from the "top" (e.g., axis 38$c$) or "side" (e.g., axis 38$b$). A sensor with six DOF can sense rotation about all three axes. A sensor with five DOF generally can sense rotation about only two of the three orientation axes.

Figure 3A:
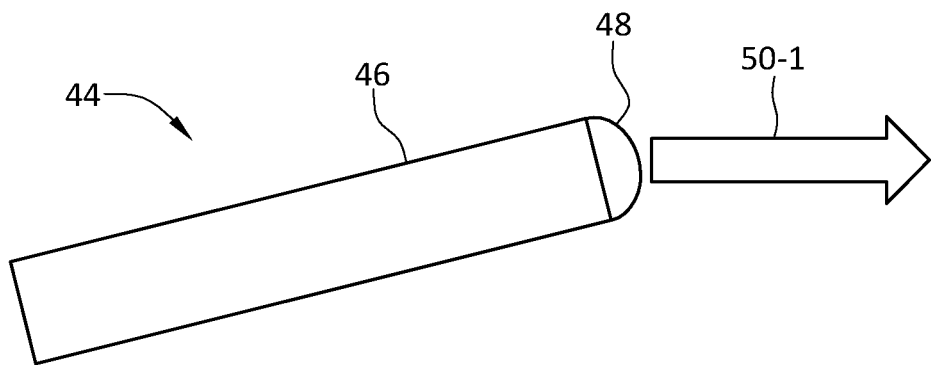
FIGS. 3A and 3B depict graphical illustrations of a force sensing medical device, in accordance with embodiments of the present disclosure.
Figure 3B:
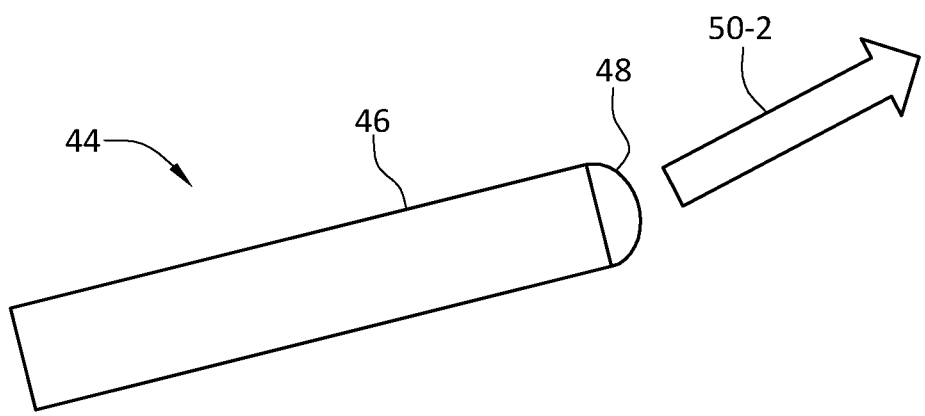

FIGS. 3A and 3B depict graphical illustrations of a force sensing medical device 44, in accordance with embodiments of the present disclosure. In some medical procedures, such as a cardiac ablation, detection and displaying of a force exerted on a distal end of a catheter (e.g., ablation head) can be useful to a physician when performing the procedure. For example, providing such information to a physician can allow a physician to ensure that a proper force is applied between the distal end of the catheter and tissue being ablated. Without contact-force sensing technology, physicians have to estimate by touch with their hands the amount of force applied to the heart wall during an ablation. If too little force is applied, effective lesions may not be created and atrial fibrillation may recur, potentially requiring additional treatments. When too much force is applied, there is a risk of tissue injury (e.g., perforation of the tissue), which can lead to serious procedure-related complications.

In some embodiments, the force exerted on the distal end of the catheter can be broken down into a lateral component and an axial component. However, with a five DOF system, a roll of the medical device 44 may not be able to be detected. Without determination of the roll information associated with the medical device 44, a particular direction of the lateral force component may not be determined. For example, although a magnitude of the lateral force component may be detected, a directional vector associated with the lateral force component may not be determinable.

In some prior approaches, the force exerted on the distal end of the catheter can be displayed to a physician via a graphical user interface. Although the direction of the axial component of the force can be displayed (e.g., aligned with the axis of the medical device), the direction of the lateral force component is not displayed, because the directional vector associated with the lateral force component has not been determined. In some of these prior approaches, a graphical depiction of force can be represented as a force diagram located distal to a graphical depiction of a medical device. As an axial force increases, an axial length of the graphical depiction of force can increase to represent the increase in force. As a lateral force increases, a lateral width of the graphical depiction of force can increase. However, this does not provide a physician with an indication of a particular direction of the axial force.

In some embodiments of the present disclosure, the roll (and/or position and orientation) of a portion of the medical device 44 can be determined via a magnetic mapping signal produced by the electromagnetic position sensor 28 that is responsive to an applied magnetic field and an electrical mapping signal produced by the plurality of electrodes 30 that is responsive to an applied electrical field. The roll of the portion of the medical device 44 can be used to determine a vector associated with the lateral component of the force exerted on the distal end of the medical device 44. Thus, the vector associated with the axial component of the force and the vector associated with the lateral component of force can be displayed to the physician, which can be beneficial in ensuring that the distal end of the medical device 44 contacts a region of tissue in an appropriate manner, for example, in an ablation procedure.

As depicted in FIGS. 3A and 3B, graphical illustrations of a force sensing medical device 44 can be displayed, in accordance with embodiments of the present disclosure. The graphical illustrations include a medical device 44, which can include an elongate catheter shaft 46 (e.g., elongate body), having a catheter tip 48, which can be representative of an ablation tip, in some embodiments. Force vectors 50-1, 50-2 can be representative of an axial force component and a lateral force component being exerted on the catheter tip 48. As depicted in FIG. 3A, a first axial force component and a first lateral force component are represented in the force vector 50-1. In FIG. 3B, a second axial force component and a second lateral force component are represented in the force vector 50-2. In comparison, the force vector 50-1 depicts the first axial force component that is of a lesser magnitude than the second axial force component depicted in force vector 50-2. For example, the force vector 50-1 is longer than the force vector 50-2.

In addition, the force vector 50-1 depicts the first lateral force component that is of a lesser magnitude and in a different direction than the second lateral force component depicted in force vector 50-2. For example, the first force vector 50-1 is depicted in a different direction than the second force vector 50-2 (representing a different directional force) and the first force vector 50-1 has a smaller cross-sectional width than the second force vector 50-2 (representing a lateral force with a lesser magnitude). Thus, determination of the roll of the medical device 44, can enable a physician to more effectively perform a medical procedure, such as ablation, by allowing for lateral force components to be determined. For instance, the physician can determine the direction in which a force is being exerted on the catheter tip 48 to more effectively create a lesion in an ablation procedure. It should be understood, however, that roll-sensing devices such as those described herein may be used in a wide variety of applications, with determination of component forces being just one such application.

Figure 4A:
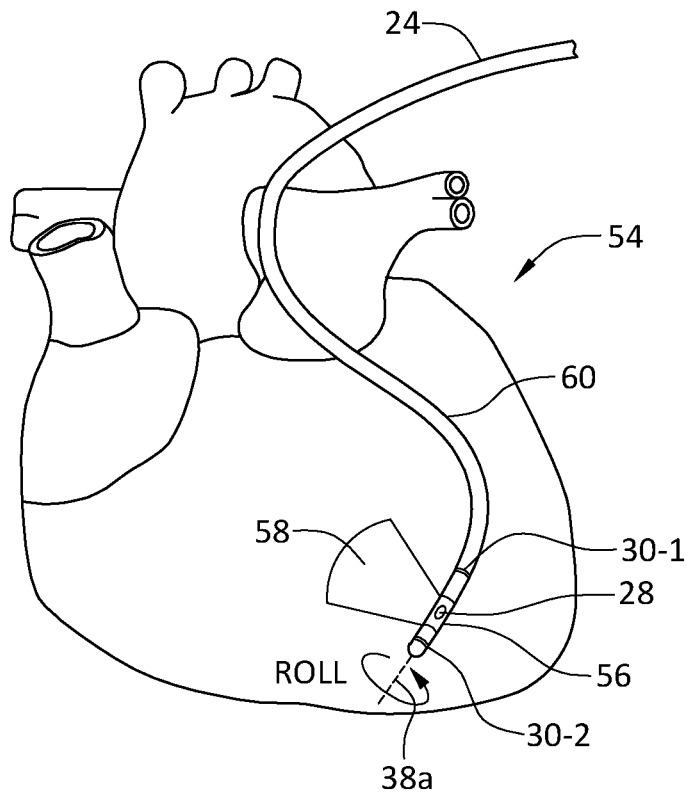
FIGS. 4A and 4B are diagrammatic views of an embodiment of a medical device disposed in a heart, in accordance with embodiments of the present disclosure.
Figure 4B:
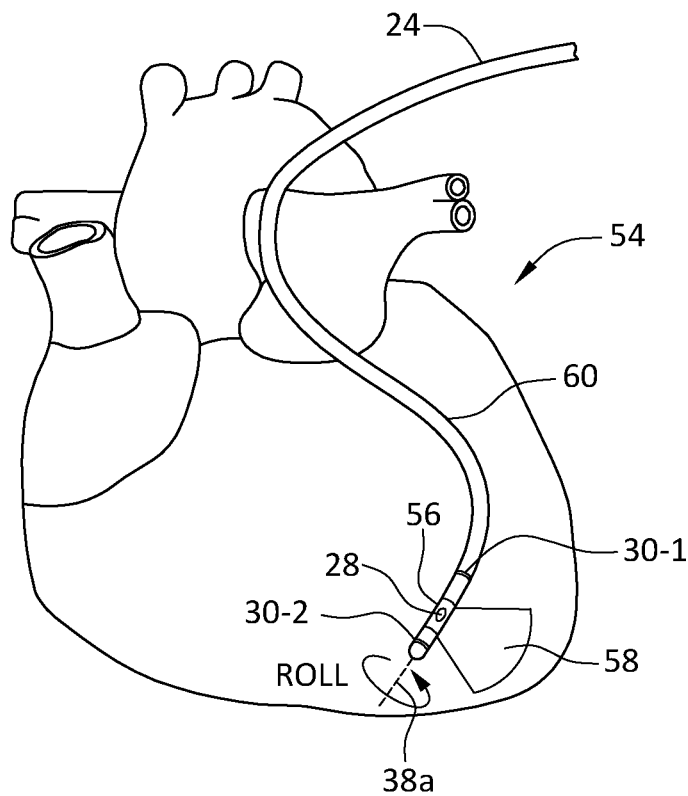

FIGS. 4A and 4B are diagrammatic views of an embodiment of a medical device 24 disposed in a heart 54, in accordance with embodiments of the present disclosure. In some embodiments, the MPS-enabled medical device 24 can be an intracardiac echocardiography (ICE) catheter with an ultrasound transducer having a particular field of view 58. In an example, the field of view 58 can be generated from one side of the ultrasound transducer 56, such that when the medical device 24 is rolled, the field of view 58 of the ultrasound transducer 56 is changed.

The medical device 24 can include electromagnetic position sensor 28 and the plurality of electrodes 30, such that the roll of an elongate shaft 60 can be determined. Thus, the 3D position (X, Y, Z) and the 3D orientation (roll, pitch, yaw) of the electromagnetic position sensor 28 and the plurality of electrodes 30 are also the 3D position and 3D orientation of the portion of medical device 24 containing electromagnetic position sensor 28 and the plurality of electrodes 30. In an example, the electromagnetic position sensor 28 and the plurality of electrodes 30 can be in substantially the same position in an elongate shaft 60 of the medical device 24 as the ultrasound transducer 56. Thus, the 3D position and 3D orientation of the electromagnetic position sensor 28 and the plurality of electrodes 30 may also be the 3D position and 3D orientation of the ultrasound transducer 56.

In an exemplary application, medical device 24 may be an ICE catheter and may be used to acquire images of the walls of the heart 54, which may then be registered with a pre-acquired model of the heart 54. To capture the images, transducer 56 transmits ultrasound waves and receives reflections of the transmitted waves from within field of view 58. The reflections are used to construct an image of anatomical structures, medical devices, and other objects within field of view 58.

To register the ultrasound images with the pre-acquired model, it is advantageous to know the orientation of field of view 58, as described in U.S. Patent Application Publication No. 2009/0163810, entitled "Sensor Guided Catheter Navigation System", with inventors Kanade et al., hereby incorporated by reference in its entirety as though fully set forth herein. As described in Kanade, ultrasound images may be more easily registered with a model of the heart if field of view 58 is known precisely with reference to positioning system coordinate system 36. If the position and orientation of field of view 58 are known, the coordinates in coordinate system 36 of each pixel and/or structure in field of view 58 can be determined without using information from the ultrasound images themselves.

As illustrated in FIGS. 4A and 4B, the medical device 24 may be rotated about longitudinal axis 38a between a first position (FIG. 4A) and a second position (FIG. 4B), for example. Accordingly, the orientation of field of view 58 can change simply by rotating transducer 56 about the axis 38a of medical device 24—e.g., the position (X, Y, Z), pitch, and yaw of transducer 56 may not change, while the roll of transducer 56 does change. In various embodiments, it may be desirable to detect such roll with fewer sensors, and by utilizing a reduced amount of space in medical device 24 with the sensor(s). A roll-sensing sensor assembly according to one or more of the embodiments described herein may be used to determine the roll associated with the medical device, such that the field of view 58 of the transducer can be determined. It should be understood, however, that roll-sensing devices such as those described herein may be used in a wide variety of applications, with intracardiac imaging being just one such application.

FIG. 5A is a schematic isometric view of an embodiment of a roll-sensing sensor assembly, in accordance with embodiments of the present disclosure. The roll-sensing sensor assembly 62 includes an electromagnetic position sensor 28a, which includes a hollow sensor core 66 and a sensor coil 68 with two free ends 70a, 70b, and a plurality of electrodes 30. Core 66 may be an elongate hollow tube extending along a central axis B' having an outer surface 72 and a central through-bore 74 extending between opposing axial ends. Bore 74 may be configured to allow roll-sensing sensor assembly 62 to be threaded on or applied to medical devices. Radially-outermost surface 72 may act as a winding surface for coil 68. In turn, coil 68 may be wound on outer surface 72 about axis B' with free coil ends 70 left exposed for use as leads in connecting coil 68 to MPS 22. It should be noted that axis B' is shown superimposed outside the surface of core 66 to illustrate the intersection of axis B' with line C', discussed in more detail below. Axis B' in fact extends through the geometric center of core 66 and of coil 68. Embodiments of the present disclosure can include additional features, as described in U.S. Patent Application Publication 2013/0169272, entitled "Roll Detection and Six Degrees of Freedom Sensor Assembly", with inventors Eichler et al., hereby incorporated by reference in its entirety as though fully set forth herein.

Core 66 may be solid or hollow (as shown), depending on the application, and may be made of, for example only, metal or polymer. Materials for core 66 may be selected for, among other things, their magnetic permeability to enhance the sensitivity of coil 68, or for the similarity of their mechanical properties to desired mechanical properties of a medical device. For example, a metal core may be desirable to increase sensitivity in a smaller-diameter device (e.g., for use in a guidewire application). Instead of a hollow core, a solid core may be used in an embodiment to reduce the size of the sensor and/or enhance the sensitivity of the sensor. Alternatively, the core 66 may be omitted entirely (e.g., an air core). Core 66 may be sized, both radially and axially, to suit a particular application.

Figure 5B:
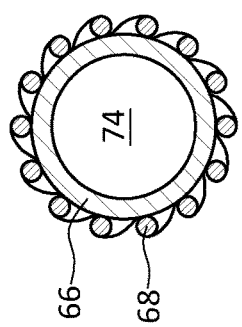
FIG. 5B is a cross-sectional view of the position sensor of FIG. 5A, in accordance with embodiments of the present disclosure.

FIG. 5B is a cross-sectional view of roll-sensing sensor assembly 62, taken substantially along line 5B-5B, which is parallel with line C'. As illustrated in FIGS. 5A and 5B, coil 68 may comprise a conductor wound in a manner, such that it radially surrounds a volume. For example, coil 68 may comprise conventional wire having suitable characteristics, such as material or alloy type, thickness (wire gauge—AWG), insulative coating type and thickness, and the like, as known in the art. Coil 68 may be wound to a desired number of loops, desired axial length, and desired radial thickness (e.g., layers) to meet desired detection characteristics. Though only one layer is shown for coil 68, more layers may be included, in an embodiment.

The plurality of electrodes 30 can be axially spaced apart along the axis B' and can be concentric with the axis B'. For example, an axis defined by the plurality of electrodes 30 can be parallel to and collinear with the axis B'. In some embodiments, the coil 68 can be located between the plurality of electrodes 30. Alternatively, the plurality of electrodes 30 can be located proximally or distally with respect to the coil 68.

The electromagnetic position sensor 28a may be configured to detect characteristics of a changing magnetic field. In an example, the coil 68 can be configured to produce a magnetic mapping signal responsive to an applied magnetic field. At the electromagnetic position sensor level, such detection is represented by a current induced through coil 68 by a local applied magnetic field. The induced current is proportional to the change in magnetic flux passing through the coil 68. Such a flux change may occur as a result of one or both of (1) a changing flux of the magnetic field itself, or (2) a change in the projected area (e.g., position or orientation) of the coil 68 in the field.

Briefly, the flux of the magnetic field itself may change according to the electrical signal provided in a field transmitting coil to create the magnetic field. As the current of the signal increases and/or decreases in amplitude (such as, for example, in a sinusoidal manner), the flux of the magnetic field changes. However, such flux changes in a medical environment will be accounted for by a processing system, such as by the MPS 22 shown in FIG. 1.

The projected area of a coil in a magnetic field is the rectilinear projection of a surface of the coil onto a plane normal to an axis of the field—that is, the two-dimensional area occupied by the volume of the coil in the normal plane. For example, if a circular coil is initially placed along an axis of a magnetic field (e.g., the normal vector of a loop of the coil (e.g., plane of symmetry of a loop) is parallel with the field axis), the projected area of the coil on that axis of the field is simply the area of the circle. But as the circular coil is turned or tilted (e.g., about an axis similar to axis 38b or 38c shown in FIG. 2), each loop in the coil has a decreasing projection onto the plane normal to the field axis. As the projected area of the coil onto an axis of the field decreases, so does the magnetic flux passing through the coil on that axis. Once the coil is turned or tilted 90 degrees from its original position, such that its normal vector is perpendicular to the field axis, its projected area is essentially zero, as is the amount of flux passing through the coil.

In some prior approaches, medical devices have included electromagnetic position sensors that comprise a coil that includes a number of loops. Each loop of the coil can lie substantially within a plane (e.g., a plane of symmetry of each loop), which may be substantially perpendicular to a longitudinal axis defined by the coil and a longitudinal axis defined by the medical device. For instance, the coil has a substantially zero winding angle relative to a line perpendicular to the longitudinal axis defined by the coil and the longitudinal axis defined by the medical device. Electromagnetically, this perpendicularity may be problematic for magnetic field-based orientation detection because in-plane rotation may not change the projected area of the loop in any axis of the magnetic field. As a result, the coil appears to a signal processing device (e.g., MPS 22 shown in FIG. 1) as having the same orientation despite rotation of the coil. Thus, in-plane rotation is not meaningfully detected by the coil. In other words, rotation about a line that is perpendicular to a plane formed by each of the loops in the coil (e.g., plane of symmetry) is a rotational "blind spot" (e.g., rotation about a longitudinal axis of the device equipped with the coil). Various embodiments described herein address such rotational blind spots for magnetic position sensors.

Figure 5C:
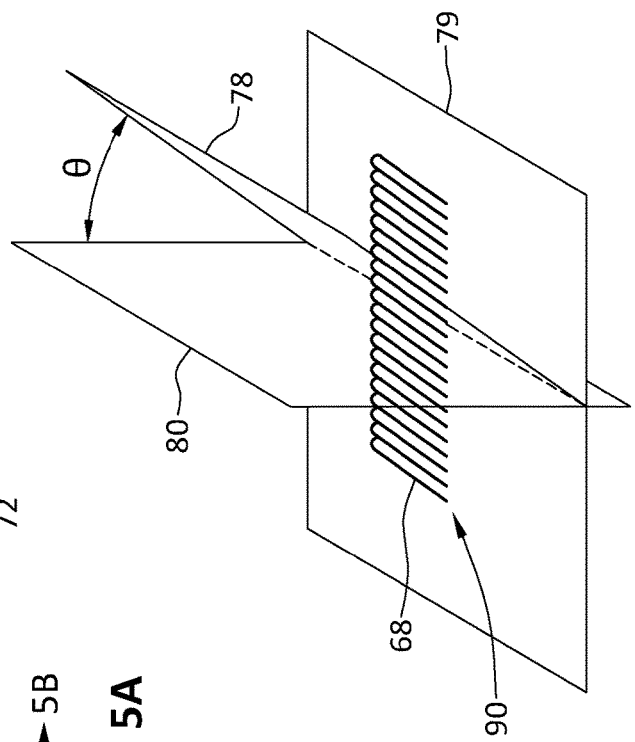
FIG. 5C is a schematic isometric view of an upper, hemi-cylindrical half of the coil depicted in FIG. 5A, in accordance with embodiments of the present disclosure.

In various embodiments described herein, rotation about longitudinal axis B' (shown in FIG. 5A) is referred to as the "roll" of the roll-sensing sensor assembly 62. A rotational blind spot for a loop of a coil may be associated with the winding angle of the coil. As used herein, a winding angle (also called a canting angle or coil winding angle) is defined as an angle at which the loops of the coil are canted or leaned (see, for example, angle θ' in FIG. 5A). FIG. 5C is a schematic, isometric view of an upper, hemi-cylindrical half of the coil 68 depicted in FIG. 5A. In FIG. 5C, two orthogonal planes 79, 80 and a canting plane 78 are visible. The hemi-cylindrical dividing plane 79 figuratively divides the coil 68 into upper and lower hemi-cylindrical coil halves (only the upper hemi-cylindrical coil half is shown in FIG. 5C). The perpendicular transverse plane 80, which figuratively cuts through the coil 68 transverse to the coil longitudinal axis B' (visible in FIG. 5A), is perpendicular to the hemi-cylindrical dividing plane 79.

The canting plane 78 (or coil plane or loop plane), which evenly bisects a full rotation of the coil 68 (i.e., a full 360° turn or rotation of the coil about the coil longitudinal axis B'), is offset or canted from the perpendicular transverse plane 80 by a winding angle θ (i.e., the winding angle θ is the angle between the transverse plane 80 and the canting plane 78). In an example, the canting plane 78 can form a plane of symmetry for a full rotation of the coil and/or can be co-planar with a plane of symmetry formed by one of the loops in the coil, evenly bisecting a full rotation of the coil. If the coil 68 has a winding angle of zero degrees, then the canting plane 78 is parallel to (or coincident with) the perpendicular transverse plane 80. Thus, the perpendicular transverse plane 80 may also evenly bisect a full 360° turn of the coil 68 about the coil longitudinal axis (e.g., form a plane of symmetry for a turn of the coil 68).

With further reference to FIG. 5A, which is an isometric side and end view of the hollow sensor core 66 with a sensor coil 68 mounted on it, the line C' is parallel with the perpendicular transverse plane 80 (and could lie within the perpendicular transverse plane 80) shown in FIG. 5C, and the longitudinal axis B' is parallel with the hemi-cylindrical dividing plane 79 (and could lie within the hemi-cylindrical dividing plane 79). The canting plane 78' (schematically depicted from the side in FIG. 5A) forms a plane of symmetry for the loop 76a in the coil 68. The winding angle is defined as the angle (e.g., θ' in FIG. 5A) formed between line C', which is perpendicular to the hemi-cylindrical dividing plane 79, and canting loop plane 78'. The line C' can be perpendicular to the longitudinal axis B' and can extend from the longitudinal axis B' through a most proximally extending portion of one of the loops of the coil 68. In roll-sensing sensor assembly 62, none of the loops 76a in the coil 68 is parallel with line C' (i.e., none of the loops 76a is parallel to or symmetric about either line C' or perpendicular transverse plane 80). For example, the loops of the coil 68 can be disposed at an angle (e.g., θ'), with respect to the line C'. In roll-sensing sensor assembly 62, therefore, the coil 68 has a nonzero winding angle.

In other words, coil 68 has a nonzero winding or canting angle θ' relative to the perpendicular line C', which is perpendicular to the longitudinal axis B' and to the hemi-cylindrical dividing plane 79. Because the coil 68 has a nonzero winding angle, a line perpendicular to a plane of symmetry of a loop in coil 68 is offset from longitudinal axis B', so the projected area of the coil in the magnetic field changes as the electromagnetic position sensor 28a rotates about longitudinal axis B'. Because the projected area changes based on the rotation of the coil, the signal produced by electromagnetic position sensor 28a responsive to the magnetic field is indicative of the roll of the roll-sensing sensor assembly 62. However, each loop in coil 68 is effectively parallel with each other loop, so electromagnetic position sensor 28a still has a rotational blind spot. So although electromagnetic position sensor 28a can detect roll, it remains a five-DOF sensor.

For example, as the electromagnetic position sensor 28a is rotated around an axis extending through the coil 68 that is perpendicular to canting plane 78', the coil can appear to MPS 22 as having the same orientation despite rotation of the coil 68, thus causing the rotational blind spot. In some embodiments, the coil 68 can be asymmetrically wound around an axis associated with the medical device, such that rotation of the medical device around a longitudinal axis of the medical device can produce an asymmetric signal as the medical device is rotated. For example, as the coil is rotated with the medical device, a signal produced by the coil can be asymmetric as the medical device and the coil are rotated.

However, embodiments of the present disclosure include a plurality of electrodes 30 disposed about the longitudinal axis B', which can detect rotation about the blind spot. The electrodes 30 can be configured to detect characteristics of a changing electrical field. In an example, the plurality of electrodes 30 can be configured to produce an electrical mapping signal responsive to an applied electrical field produced by the electrode patches. Such detection is represented by a current induced through electrodes by a local applied electrical field. The induced current is proportional to the change in position of the electrodes 30 with respect to the electrical field. The electrical field itself may change according to the electrical signal provided in the electrode patches to create the electrical field. As the electrodes 30 are turned or tilted (e.g., about an axis similar to axis 38b or 38c shown in FIG. 2) an electrical mapping signal responsive to the applied electrical field can be varied, because the electrodes 30 are exposed to varying strengths of the electrical field.

In an example, as the roll-sensing sensor assembly 62 is rotated about the rotational blind spot, the electrodes are turned or tilted, as discussed herein, thus creating varying electrical mapping signals. Thus, in combination, the magnetic mapping signal produced by the electromagnetic position sensor 28a and the electrical mapping signals produced by the electrodes 30 are indicative of at least a roll of the roll-sensing sensor assembly 62 (e.g., the magnetic mapping signal and the electrical mapping signals are indicative of a full six degrees-of-freedom). For example, signals from two five DOF sensors can be combined to form a six DOF sensor assembly (e.g., roll-sensing sensor assembly 62). The magnetic mapping signal and the electrical mapping signals can be processed (e.g., by MPS 22) to determine the six-DOF P&O of the roll-sensing sensor assembly 62.

The winding angle θ' of coil 68 may be varied in different embodiments to, for example, maximize the sensor's ability to detect roll but still minimize the axial size of the sensor. The winding angle should be nonzero—i.e., large enough that the projected area of the coil in the magnetic field meaningfully changes as the sensor rolls such that a processor or electronic control unit such as, for example only, MPS 22 shown in FIG. 1, can determine the roll of the coil 68 according to the change in projected area. The exact angle needed for such a "meaningful" change may vary depending on characteristics of the sensor (e.g., materials, coil diameter, etc.) and/or the system (e.g., magnetic field strength, signal processing resolution, signal-to-noise ratio).

In one exemplary combination of sensor and system, the projected area of the coil 68 in the magnetic field meaningfully changes with a winding angle θ' of the coil 68 that is at least about 2 degrees. Accordingly, in an embodiment, a winding angle θ' of coil 68 may be considered "nonzero" if it is at least 2 degrees, though "nonzero" is not necessarily limited to such an angle. In an embodiment, coil 68 may achieve maximum resolution for roll detection with a winding angle θ' of about 90 degrees. Accordingly, in various embodiments, the winding angle θ' may be between about 2 degrees and about 90 degrees or between about 2 degrees and about 45 degrees. In some embodiments, the winding angle θ' may be between about 30 degrees and about 60 degrees. In some embodiments, the winding angle θ' may be between about 40 degrees and about 50 degrees. In some embodiments, the winding angle θ' may be about 45 degrees. It should be understood that the foregoing winding angles are exemplary only, and not limiting in nature except as may be recited in the claims.

FIG. 6 is a side view of a medical device 24 comprising a roll-sensing sensor assembly 84, in accordance with embodiments of the present disclosure. In some examples, the medical device 24 can be a catheter for use in a medical procedure, such as mapping or ablation. In some embodiments, the medical device 24 can include an irrigated or a non-irrigated catheter tip. The medical device 24 can include an elongate catheter shaft 86 (e.g., elongate body), having a proximal end and a distal end. The proximal end can be connected to a catheter handle (not shown), and the distal end can be connected to a catheter tip 88. The medical device 24 can include a first longitudinal axis B", that extends along a longitudinal length of the elongate catheter shaft 86. In some embodiments, a plurality of electrodes 30 can be disposed about the first longitudinal axis B", and can be configured to produce an electrical mapping signal responsive to an applied electrical field. In an example, the electrodes can be ring electrodes that are concentric with the first longitudinal axis B".

The medical device 24 can include an electromagnetic position sensor 90, as discussed herein, that extends along and is disposed about a second axis. The electromagnetic position sensor 90 can include a coil 94 that is wound around a core 92, which can be formed from materials that have a magnetic permeability that enhance a sensitivity of the coil 94 to an applied magnetic field. Alternatively, the core 92 may be omitted entirely, and the coil 94 can be wrapped around the elongate catheter shaft 86. In some embodiments, and as depicted in FIG. 6, the second axis can be parallel and collinear with the first longitudinal axis B". Thus, the coil 94 can be concentrically wrapped around the first longitudinal axis B".

The coil 94 can be axially spaced apart from the plurality of electrodes along the elongate shaft 86 of the catheter. As depicted in FIG. 6, the coil 94 can be axially located between electrode 30-1 and electrode 30-2. However, all of the electrodes 30 can be axially located proximally with respect to the coil 94, in some embodiments. Alternatively, all of the electrodes 30 can be axially located distally with respect to the coil 94, in some embodiments. In addition, multiple electrodes 30 can be axially located proximally with respect to the coil 94 and distally with respect to the coil 94. In some embodiments, a single electrode 30 can be axially located proximally with respect to the coil 94 and multiple electrodes 30 can be axially located distally with respect to the coil 94. In some embodiments, as depicted in FIG. 6, the electrodes 30 can be axially spaced apart from one another.

In some embodiments, the coil 94 can comprise a winding angle θ" that is nonzero relative to a line perpendicular (e.g., perpendicular axis C") to the first longitudinal axis (e.g., longitudinal axis B") and second axis, when the first and second axis are parallel and collinear. In an example, as discussed in relation to FIG. 5A, a canting plane 78" can form a plane of symmetry for a loop 95 in the coil 94, evenly bisecting a full rotation of the coil 94. The canting plane 78" can extend from an intersection of a perpendicular transverse plane and a hemi-cylindrical dividing plane. The perpendicular axis C" can be parallel with the perpendicular transverse plane and normal to the hemi-cylindrical dividing plane. The first elongated axis B" can be parallel with the hemi-cylindrical dividing plane. The canting plane 78" for the loop 95 of the coil 94 can define a plane that is at a nonzero angle (e.g., θ") relative to the perpendicular transverse plane and a line perpendicular to and extending from the first elongated axis B" (e.g., perpendicular axis C").

As discussed herein, the perpendicular axis C" can extend from the first elongated axis B" through a most proximal portion of one of the loops of the coil 94. Because the coil 94 has a nonzero winding angle θ", a line perpendicular to a loop 95 in coil 94 (e.g., perpendicular or normal to the canting plane 78" for loop 95) and extending from a central origin of loop 95 is offset from axis B", so the projected area of the coil in the magnetic field changes as the electromagnetic position sensor 90 rotates about axis B". As discussed herein, because the projected area changes based on the rotation of the coil 94, a signal produced by electromagnetic position sensor 90 responsive to the magnetic field is indicative of the roll of the roll-sensing sensor assembly 84. Although the electromagnetic position sensor 90 still has a rotational blind spot, because each loop in the coil 94 is effectively parallel with each other loop, embodiments of the present disclosure include a plurality of electrodes 30 disposed about the axis B", which can detect rotation about the blind spot. The electromagnetic position sensor 90 produces a magnetic mapping signal responsive to an applied magnetic field and the electrodes 30 produce electrical mapping signals responsive to an applied electrical field. In combination, the magnetic mapping signal produced by the electromagnetic position sensor 90 and the electrical mapping signals produced by the electrodes 30 are indicative of at least a roll of the roll-sensing sensor assembly 84 (e.g., the magnetic mapping signal and the electrical mapping signals are indicative of a full six degrees-of-freedom). The roll of the medical device 24 can thus be determined.

In some embodiments, the MPS enabled medical device 24 can include sensors that are non-linearly dependent with respect to one another. In some embodiments, the electromagnetic position sensor 90 can be non-linearly dependent with respect to the electrodes 30. In an example, the electromagnetic position sensor 28a can have a nonzero winding angle θ" with respect to the first elongated axis B" and the electrodes 30 can be concentric and coaxial with the first elongated axis B". Some prior approaches have employed sensors that are linearly dependent, which can produce data that is linearly dependent, for example. Such data may be duplicative and may not be analyzed to determine a P&O expressed with six DOF. For example, a coil disposed along an axis with a zero winding angle θ" can generate P&O data that includes a 3D position (e.g., a coordinate in three axes X, Y, and Z) and 2D orientation (e.g., pitch and yaw).

Electrodes that are coaxial with the coil can also generate duplicative P&O data that includes 3D position and 2D orientation. As such, six DOF may not be extracted from the data. In contrast, the electromagnetic position sensor 28a and the electrodes 30 of the present disclosure can produce data that is non-linearly dependent. For example, the electromagnetic position sensor 28a can generate P&O data that includes a 3D position (e.g., a coordinate in three axes X, Y, and Z) and 3D orientation (e.g., roll, pitch, and yaw). In addition, the electrodes 30 can generate duplicative P&O data that includes 3D position and 2D orientation. Thus, six DOF can be provided via the data received from the electromagnetic position sensor 28a and the electrodes 30 of the present disclosure, which can each individually provide P&O data expressed with five DOF.

For example, in some embodiments, a plurality of electrodes 30 can be coupled to the elongate catheter shaft 86 (e.g., elongate body) and can be configured to produce a first position and orientation signal indicative of five degrees of freedom in response to an applied electrical field. An electromagnetic position sensor 90 (e.g., electromagnetic sensor) can be coupled to the catheter shaft 86 and can be configured to produce a second position and orientation signal indicative of five degrees of freedom in response to an applied magnetic field. In some embodiments, the first and second position and orientation signals can be combinable to determine a position and orientation indicative of six degrees of freedom. In some embodiments, as discussed herein, a computing device can determine the position and orientation indicative of six degrees of freedom from the first and second position and orientation signals (e.g., each of which are indicative of five degrees of freedom).

In some embodiments, the electrodes 30 can radially extend from the elongate shaft 86 past the coil 94. An outer sheath 98, represented by dotted lines, can be placed over the elongate shaft 86, such that an outer surface of the electrodes 30 remains exposed and the coil 94 is covered by the outer sheath.

FIG. 7 is a side view of another embodiment comprising a roll-sensing sensor assembly 114, in accordance with embodiments of the present disclosure. In some embodiments, a medical device 24, which can include an irrigated catheter tip (illustrated in FIG. 8) or a non-irrigated catheter tip 112, can comprise an elongate catheter shaft 118 (e.g., elongate body) having a first elongated axis B'''. A plurality of electrodes can be disposed about the first elongated axis B''', and can be configured to produce an electrical mapping signal responsive to an applied electrical field. The medical device 24 can include an electromagnetic position sensor 106, as discussed herein, that extends along and is disposed about a second axis D. In some embodiments, the second axis D can be disposed at a placement angle $\theta'''$ that is nonzero relative to the first elongated axis B''' (e.g., a non-zero angle can exist between the second axis D and the first elongated axis B'''). Further, the second axis D can be disposed at a placement angle. The electromagnetic position sensor 106 can include a coil 110 (e.g., electromagnetic sensor) that is wound around a core 108. In some embodiments, the core 108 can be made from a ferromagnetic material. For instance, the core 108 can be made of ferrite. The core 108 can have a core outer surface and the coil 110 can be disposed on the core outer surface.

The placement angle $\theta'''$ of the second axis D (about which the coil 110 is disposed) may be varied in different embodiments to, e.g., maximize the sensor's ability to detect roll but still minimize the axial size of the sensor. The placement angle $\theta'''$ should be nonzero—i.e., large enough that the projected area of the coil in the magnetic field meaningfully changes as the sensor rolls such that a processor or electronic control unit such as, for example only, MPS 22 shown in FIG. 1, can determine the roll of the coil 110 according to the change in projected area. The exact angle needed for such a "meaningful" change may vary depending on characteristics of the sensor (e.g., materials, coil diameter, etc.) and/or the system (e.g., magnetic field strength, signal processing resolution, signal-to-noise ratio). In one exemplary combination of sensor and system, the projected area of the coil in the magnetic field meaningfully changes with a placement angle $\theta'''$ of the coil 110 that is at least about 2 degrees. Accordingly, in an embodiment, a winding angle of coil 110 may be considered "nonzero" if it is at least two degrees, though "nonzero" is not necessarily limited to such an angle.

In an embodiment, coil 110 may achieve maximum resolution for roll detection with a placement angle $\theta'''$ of about 90 degrees. Accordingly, in various embodiments, the placement angle $\theta'''$ may be between about 2 degrees and about 90 degrees or between about 2 degrees and about 45 degrees. In some embodiments, the placement angle $\theta'''$ may be between about 30 degrees and about 60 degrees. In some embodiments, the placement angle $\theta'''$ may be between about 40 degrees and about 50 degrees. In some embodiments, the placement angle $\theta'''$ may be about 45 degrees. It should be understood that the foregoing placement angles $\theta'''$ are exemplary only, and not limiting in nature except as may be recited in the claims.

The coil 110 can extend along and be disposed about the second axis D and a winding angle of the coil 110 can be substantially zero, with respect to the second axis D. With reference to the embodiments discussed in FIGS. 5A-6, a nonzero winding angle of the coil 110 allows a roll of the catheter to be detected. However, with respect to the embodiments depicted in FIG. 7, by winding the coil 110 at a substantially zero winding angle about the second axis, with respect to the second axis, a loop of the coil 110 can define a plane (e.g., canting plane) that is nonzero relative to a line perpendicular to and extending from the first elongated axis B''' (e.g., perpendicular axis C'''). The perpendicular axis C''' can extend through a most proximal portion of one of the loops of the coil 110, as discussed herein. This effectively gives the coil 110 a nonzero winding angle with respect to the first elongated axis B'''. In other words, a line perpendicular to the canting plane of a loop in coil 110 and extending from a central origin of the loop in coil 110 (e.g., second axis D) is offset from the first elongated axis B''', so the projected area of the coil 110 in the magnetic field changes as the electromagnetic position sensor 106 (and the medical device 24) rotates about axis B'''.

As discussed herein, because the projected area changes based on the rotation of the coil 110, a signal produced by electromagnetic position sensor 106 responsive to the magnetic field is indicative of the roll of the roll-sensing sensor assembly 114. Although the electromagnetic position sensor 106 still has a rotational blind spot, because each loop in the coil 110 is effectively parallel with each other loop, embodiments of the present disclosure include a plurality of electrodes 30 disposed about the axis B''', which can detect rotation about the blind spot. The electromagnetic position sensor 106 produces a magnetic mapping signal responsive to an applied magnetic field and the electrodes 30 produce electrical mapping signals responsive to an applied electrical field. In combination, the magnetic mapping signal produced by the electromagnetic position sensor 106 and the electrical mapping signals produced by the electrodes 30 are indicative of at least a roll of the roll-sensing sensor assembly 114 (i.e., the magnetic mapping signal and the electrical mapping signals are indicative of a full six degrees-of-freedom). The roll of the medical device 24 can thus be determined.

As discussed in relation to FIG. 6, in some embodiments, the electrodes 30 can radially extend from the elongate shaft 118 past the coil 110. An outer sheath 116, represented by dotted lines, can be placed over the elongate shaft 118, such that outer surfaces of the electrodes 30 remain exposed and the coil 110 is covered by the outer sheath. In some embodiments, the medical device 24 can comprise an irrigated or a non-irrigated catheter tip, in some embodiments.

In some embodiments, the electromagnetic position sensor 106 can be located within a central lumen of the elongate catheter shaft 118. Alternatively, the electromagnetic position sensor 106 can be connected to an outer surface of the elongate catheter shaft 118. In an example, the electromagnetic position sensor 106 can be located within an annular space defined by an outer surface of the outer sheath 116 and an outer surface of the elongate catheter shaft 118 (e.g., the space between the outer surface of the elongate catheter shaft and the outer sheath 116). Thus, space within the central lumen of the elongate catheter shaft 118 can be preserved for irrigation lines, electrical lines, pull wires, etc. However, the outer sheath 116 can still cover the electromagnetic position sensor 106, ensuring a smooth and uninterrupted outer surface of the medical device 24.

FIG. 8 is a isometric view of an embodiment similar to that shown in FIG. 7, in accordance with embodiments of the present disclosure. In some embodiments, a medical device 120 can include an elongate shaft. One or more pull wires 126-1, 126-2 can pass through the elongate shaft, which can be configured to provide for deflection of the elongate shaft. In addition, one or more wires 128-1, 128-2 can pass through the elongate shaft to provide electrical connections for a sensor, an ablation tip, etc. In addition, a fluid line 130 can pass through the elongate shaft to provide for a flow of irrigation fluid to an irrigated catheter tip 140 (e.g., ablation tip).

In some embodiments, the catheter tip 140 can be connected to the elongate shaft via a catheter tip connector 132. The catheter tip connector 132 can be connected to the catheter tip 140 and to a stiffening member 134, in an example. The stiffening member 134 can be formed out of metal, in some embodiments, and can include one or more attachment points for pull wires 126-1, 126-2. The stiffening member 134 can include a proximal radial ridge 136 and a distal radial ridge 138 that have diameters that are greater than a diameter of a central portion of the stiffening member 134, as depicted in FIG. 8. In some embodiments, the electromagnetic position sensor 124 can be connected to one of the radial ridges. For instance, as depicted in FIG. 8, the electromagnetic position sensor 124 can be connected to the proximal radial ridge 136.

As discussed in relation to FIG. 7, the electromagnetic position sensor 124 can be disposed along an axis D' that is disposed at a placement angle that is nonzero relative to an axis B'''' defined by the elongate shaft. In some embodiments, the electromagnetic position sensor 124 can be connected to the central portion of the stiffening member 124 and can be disposed along an axis that is disposed at a placement angle that is nonzero relative to an axis B'''' defined by the elongate shaft. Although not shown in FIG. 8, a plurality of electrodes can be disposed about the axis B'''' defined by the elongate shaft in a manner similar to that discussed in relation to FIGS. 5A, 6, and 7.

The coil can be disposed about the axis D' with a substantially zero winding angle, with respect to the axis D'. As such, by winding the coil at a substantially zero winding angle about the axis D', a loop of the coil can define a plane that is nonzero relative to a line perpendicular to the axis B''''. Accordingly, as discussed in relation to FIG. 7, the roll of the catheter can be determined based on a combination of signals produced by the electrodes and the coil.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of a roll-sensing sensor assembly has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device comprising:
   an elongate body defining a first axis;
   a plurality of electrodes disposed about the first axis;
   a coil extending along and disposed about a second axis, wherein:
   a canting plane of a loop in the coil is nonzero relative to a line perpendicular to and extending from the first axis
   the plurality of electrodes are disposed proximally and distally with respect to the coil, and
   a computing device is in communication with the plurality of electrodes and the coil wherein the computing device is configured to determine a roll of the elongate body, based on a combination of an electrical mapping signal produced by the plurality of electrodes responsive to an applied electrical field and a magnetic mapping signal produced by the electromagnetic sensor responsive to an applied magnetic field.

2. The medical device of claim 1, wherein the second axis is disposed at a placement angle that is nonzero relative to the first axis.

3. The medical device of claim 2, wherein a winding angle of the coil extending along and disposed about the second axis is substantially zero, with respect to the second axis.

4. The medical device of claim 3, wherein the coil extending along and disposed about the second axis is configured to produce a magnetic mapping signal responsive to an applied magnetic field indicative of at least a roll of the coil about the first axis.

5. The medical device of claim 3, further comprising a core extending along the second axis having a core outer surface, wherein the coil is disposed on the core outer surface.

6. The medical device of claim 5, wherein the core comprises a ferromagnetic material.

7. The medical device of claim 1, wherein the second axis and the first axis are collinear.

8. The medical device of claim 7, wherein the coil comprises a winding angle that is nonzero relative to a line perpendicular to the first and second axes.

9. The medical device of claim 8, wherein the coil is configured to produce a magnetic mapping signal responsive to an applied magnetic field indicative of at least a roll of the coil about the first and second axes.

10. The medical device of claim 1, wherein the coil is axially spaced apart from the plurality of electrodes along the elongate catheter having the first axis.

11. A medical device sensor assembly comprising: a plurality of electrodes disposed about an axis; and a coil extending along and disposed about the axis, wherein:
   the coil comprises a winding angle that is nonzero relative to a line perpendicular to and extending from the axis, the plurality of electrodes are disposed proximally and distally with respect to the coil, and
   a computing device is in communication with the plurality of electrodes and the coil wherein the computer is configured to determine a roll of the medical device, based on a combination of an electrical mapping signal produced by the plurality of electrodes responsive to an applied electrical field and a magnetic mapping signal produced by the electromagnetic sensor responsive to an applied magnetic field.

12. The medical device sensor assembly of claim 11, wherein the coil radially surrounds a volume through which the axis extends.

13. The medical device sensor assembly of claim 11, further comprising a core extending along the axis having a core outer surface, wherein the coil is disposed on the core outer surface.

14. The medical device sensor assembly of claim 11, wherein:
   the coil is configured to produce a magnetic mapping signal responsive to an applied magnetic field;
   the plurality of electrodes are configured to produce an electrical mapping signal responsive to an applied electrical field; and
   the magnetic mapping signal and the electrical mapping signal are indicative of at least a roll of the medical device sensor assembly.

15. A medical device sensor assembly, comprising:
   an elongate catheter having a first axis;
   a plurality of electrodes disposed about the first axis, the plurality of electrodes coupled with a processor;
   an electromagnetic sensor extending along and disposed about a second axis, the electromagnetic sensor coupled with the processor, wherein the second axis is disposed at a placement angle that is nonzero relative to the first axis and less than 90 degrees relative to the first axis, wherein a roll of the elongate catheter is determined by the processor, based on a combination of an electrical mapping signal produced by the plurality of electrodes responsive to an applied electrical field and a magnetic mapping signal produced by the electromagnetic sensor responsive to an applied magnetic field.

16. The medical device sensor assembly of claim 15, wherein the electromagnetic sensor comprises a winding angle that is substantially zero relative to the second axis.

17. The medical device sensor assembly of claim 15, further comprising a ferromagnetic core extending along the second axis, wherein the electromagnetic sensor is disposed about an outer surface of the ferromagnetic core.

18. The medical device sensor assembly of claim 15, wherein the placement angle is in a range of 2 to 45 degrees.

19. The medical device sensor assembly of claim 15, wherein the electromagnetic sensor is located within a central lumen of the elongate catheter.

20. A medical device, comprising:
   an elongate body;
   a plurality of electrodes coupled to the elongate body and configured to produce a first position and orientation signal indicative of five degrees of freedom in response to an applied electrical field; and
   an electromagnetic sensor coupled to the elongate body and configured to produce a second position and orientation signal indicative of five degrees of freedom in response to an applied magnetic field, wherein a computing device combines the first and second position and orientation signals and determines a position and orientation indicative of six degrees of freedom.

\* \* \* \* \*